United States Patent
Klemm et al.

(10) Patent No.: US 11,511,048 B2
(45) Date of Patent: Nov. 29, 2022

(54) DRUG DELIVERY DEVICE WITH REMOVABLY ATTACHABLE SENSOR DEVICE

(71) Applicant: Sanofi-Aventis Deutschland GMBH, Frankfurt am Main (DE)

(72) Inventors: Thomas Klemm, Frankfurt am Main (DE); Alexander Allerdings, Frankfurt am Main (DE); Markus Ploch, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 181 days.

(21) Appl. No.: 16/060,501

(22) PCT Filed: Dec. 9, 2016

(86) PCT No.: PCT/EP2016/080500
§ 371 (c)(1),
(2) Date: Jun. 8, 2018

(87) PCT Pub. No.: WO2017/098006
PCT Pub. Date: Jun. 15, 2017

(65) Prior Publication Data
US 2018/0361076 A1    Dec. 20, 2018

(30) Foreign Application Priority Data
Dec. 10, 2015 (EP) ..................................... 15199192

(51) Int. Cl.
*A61M 5/31* (2006.01)
*A61M 5/315* (2006.01)

(52) U.S. Cl.
CPC .......... *A61M 5/31553* (2013.01); *A61M 5/31* (2013.01); *A61M 5/31526* (2013.01);
(Continued)

(58) Field of Classification Search
CPC ........ A61M 5/3155; A61M 2005/3125; A61M 5/31568; A61M 2205/3313;
(Continued)

(56) References Cited

U.S. PATENT DOCUMENTS 7,974,010 B2 * 7/2011 Walter .................. C09C 1/0018
359/562
8,512,296 B2   8/2013 Gabriel et al.
(Continued)

FOREIGN PATENT DOCUMENTS

CN    102112048    6/2011
CN    102413854    4/2012
(Continued)

OTHER PUBLICATIONS

International Search Report and Written Opinion in International Application No. PCT/EP2016/080500, dated Jun. 12, 2018, 10 pages.
(Continued)

*Primary Examiner* — Rebecca E Eisenberg
*Assistant Examiner* — Anna E Goldberg-Richmeier
(74) *Attorney, Agent, or Firm* — Fish & Richardson P.C.

(57) ABSTRACT

The present disclosure relates to a drug delivery device for setting and injecting of a dose of an injectable medicament, the drug delivery device comprising: an elongated housing extending along a longitudinal axis and having a sidewall with at least a first aperture, at least one number sleeve rotatably supported inside the housing and comprising an outer surface, wherein a first portion of the outer surface is visible through the first aperture and wherein the number sleeve comprises a non-visible code in the region of the first portion.

17 Claims, 12 Drawing Sheets

(52) U.S. Cl.
CPC . *A61M 5/31551* (2013.01); *A61M 2005/3126* (2013.01); *A61M 2205/0227* (2013.01); *A61M 2205/0238* (2013.01); *A61M 2205/3313* (2013.01); *A61M 2205/3317* (2013.01); *A61M 2205/502* (2013.01); *A61M 2205/583* (2013.01); *A61M 2205/585* (2013.01); *A61M 2205/6063* (2013.01)

(58) Field of Classification Search
CPC .. A61M 2205/6072; A61M 2039/0045; A61M 5/31533
See application file for complete search history.

(56) References Cited

U.S. PATENT DOCUMENTS

| | | | |
|---|---|---|---|
| 9,522,238 B2 * | 12/2016 | Nielsen | A61M 5/31556 |
| 9,764,095 B2 * | 9/2017 | Draper | A61M 5/31525 |
| 10,004,852 B2 * | 6/2018 | Marsh | A61M 5/3155 |
| 2010/0274198 A1 * | 10/2010 | Bechtold | A61M 5/31551 604/189 |
| 2011/0313365 A1 | 12/2011 | Wieselblad | |
| 2012/0043377 A1 | 2/2012 | Haar et al. | |
| 2013/0072897 A1 * | 3/2013 | Day | G06K 7/10 604/500 |
| 2020/0175640 A1 * | 6/2020 | Meier | G06T 1/0014 |

FOREIGN PATENT DOCUMENTS

| | | |
|---|---|---|
| CN | 102725011 | 10/2012 |
| CN | 103702699 | 4/2014 |
| CN | 104902944 | 9/2015 |
| EP | 2708253 | 3/2014 |
| JP | 2008-537491 | 9/2008 |
| JP | 2009-538937 | 11/2009 |
| JP | 2011-530129 | 12/2011 |
| JP | 2013-517817 | 5/2013 |
| JP | 2013-521963 | 6/2013 |
| JP | 2014-520584 | 8/2014 |
| JP | 2016-502899 | 2/2016 |
| JP | 2016-518901 | 6/2016 |
| WO | WO 2006/083933 | 8/2006 |
| WO | WO 2007/137438 | 12/2007 |
| WO | WO 2008/145171 | 12/2008 |
| WO | WO 2011/089205 | 7/2011 |
| WO | WO 2011/117212 | 9/2011 |
| WO | WO 2013/004844 | 1/2013 |
| WO | WO-2013004844 A1 * | 1/2013 ......... G06F 19/3456 |
| WO | WO 2013/110538 | 8/2013 |
| WO | WO 2014/064691 | 5/2014 |
| WO | WO 2014/111336 | 7/2014 |
| WO | WO 2014/111340 | 7/2014 |
| WO | WO 2014/166922 | 10/2014 |
| WO | WO 2014/173775 | 10/2014 |
| WO | WO-2017081051 A1 * | 5/2017 ......... A61M 5/31568 |

OTHER PUBLICATIONS

International Preliminary Report on Patentability in International Application No. PCT/EP2016/080500, dated Mar. 20, 2017, 13 pages.

* cited by examiner

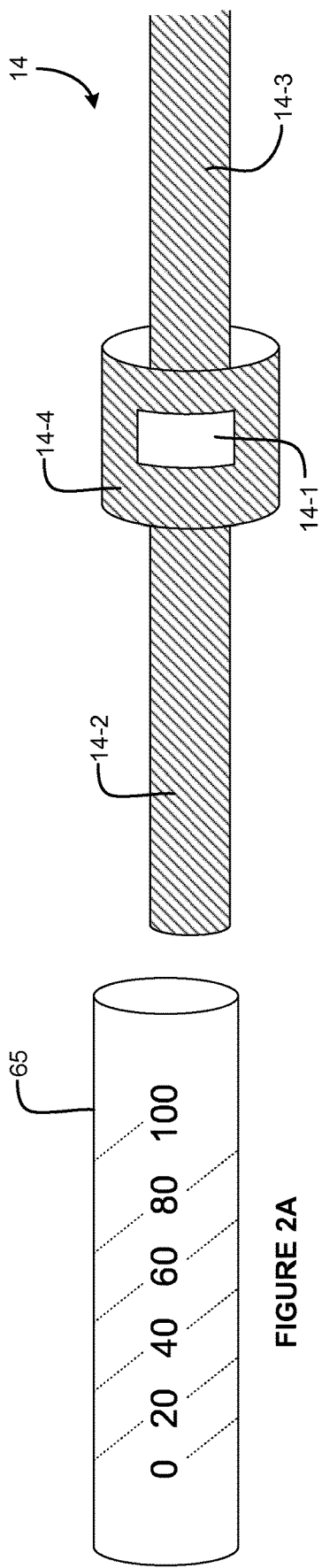
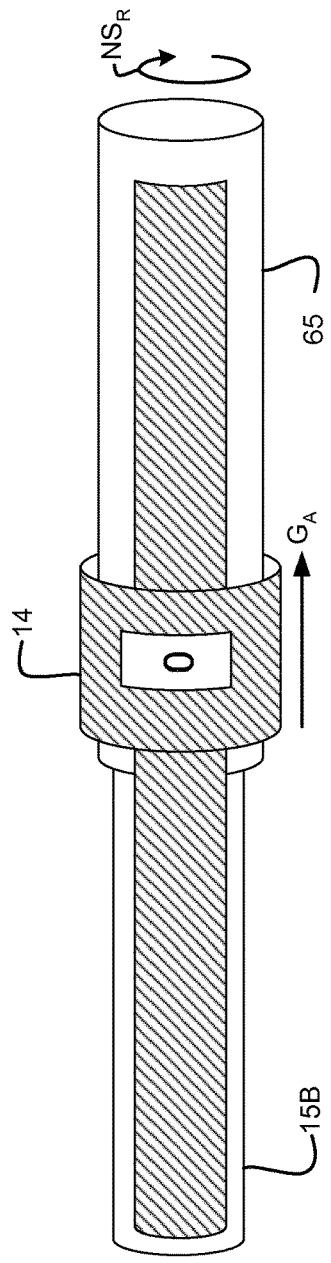
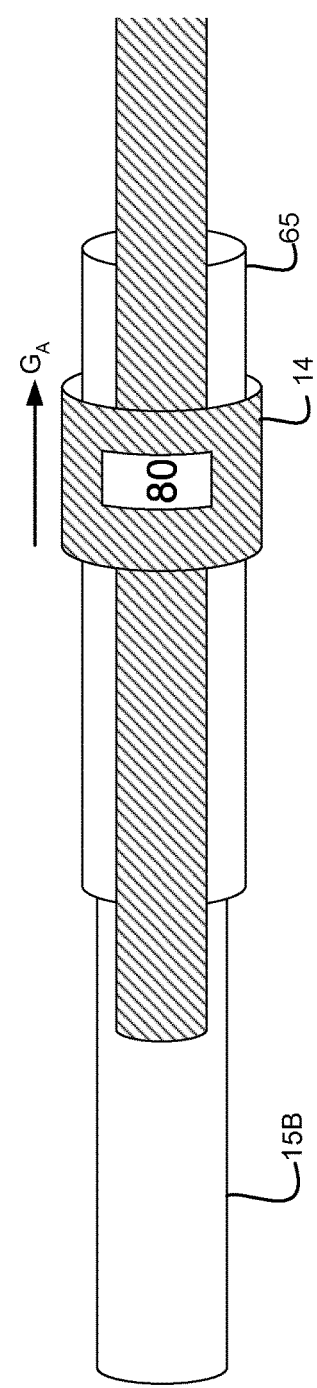

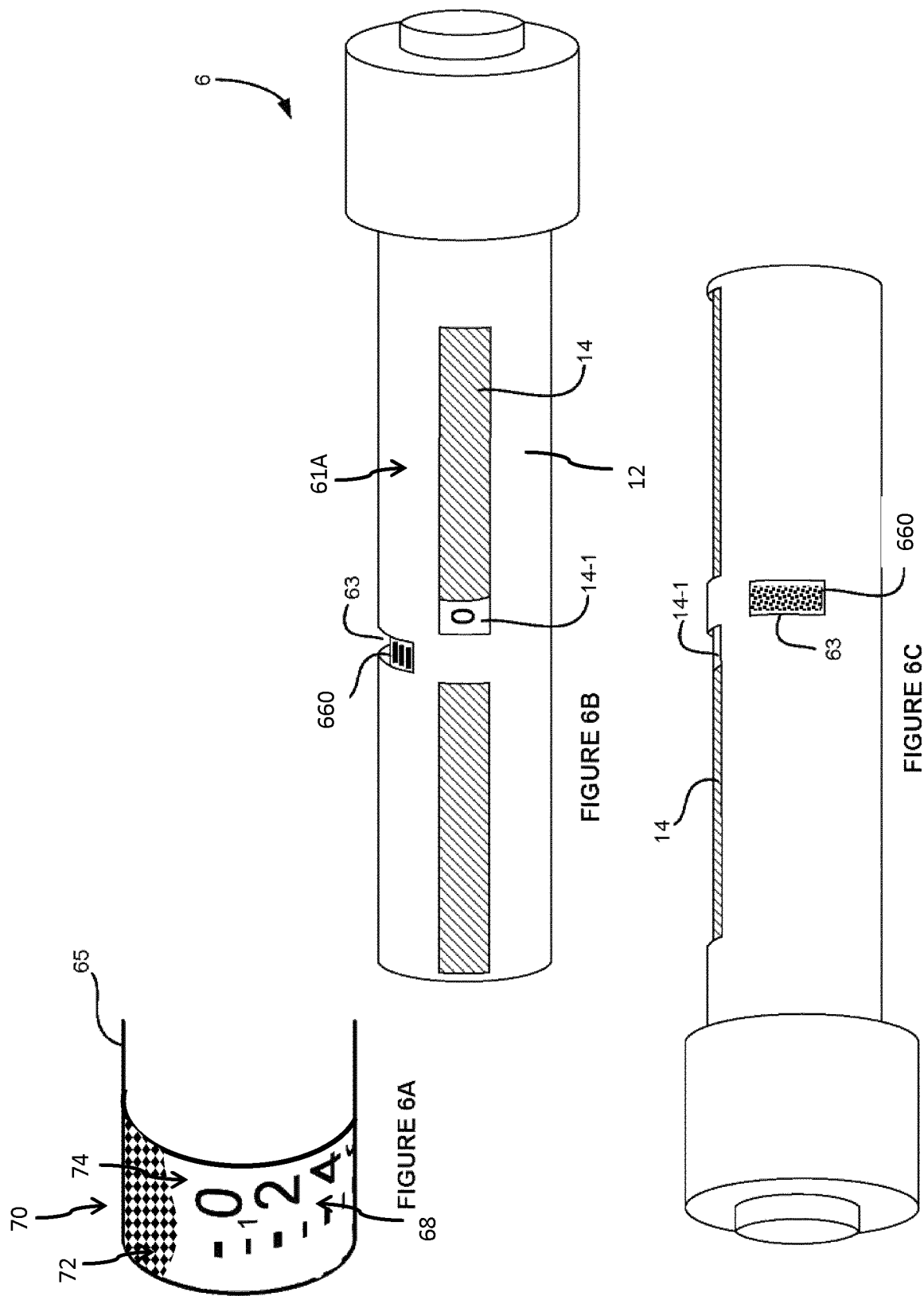

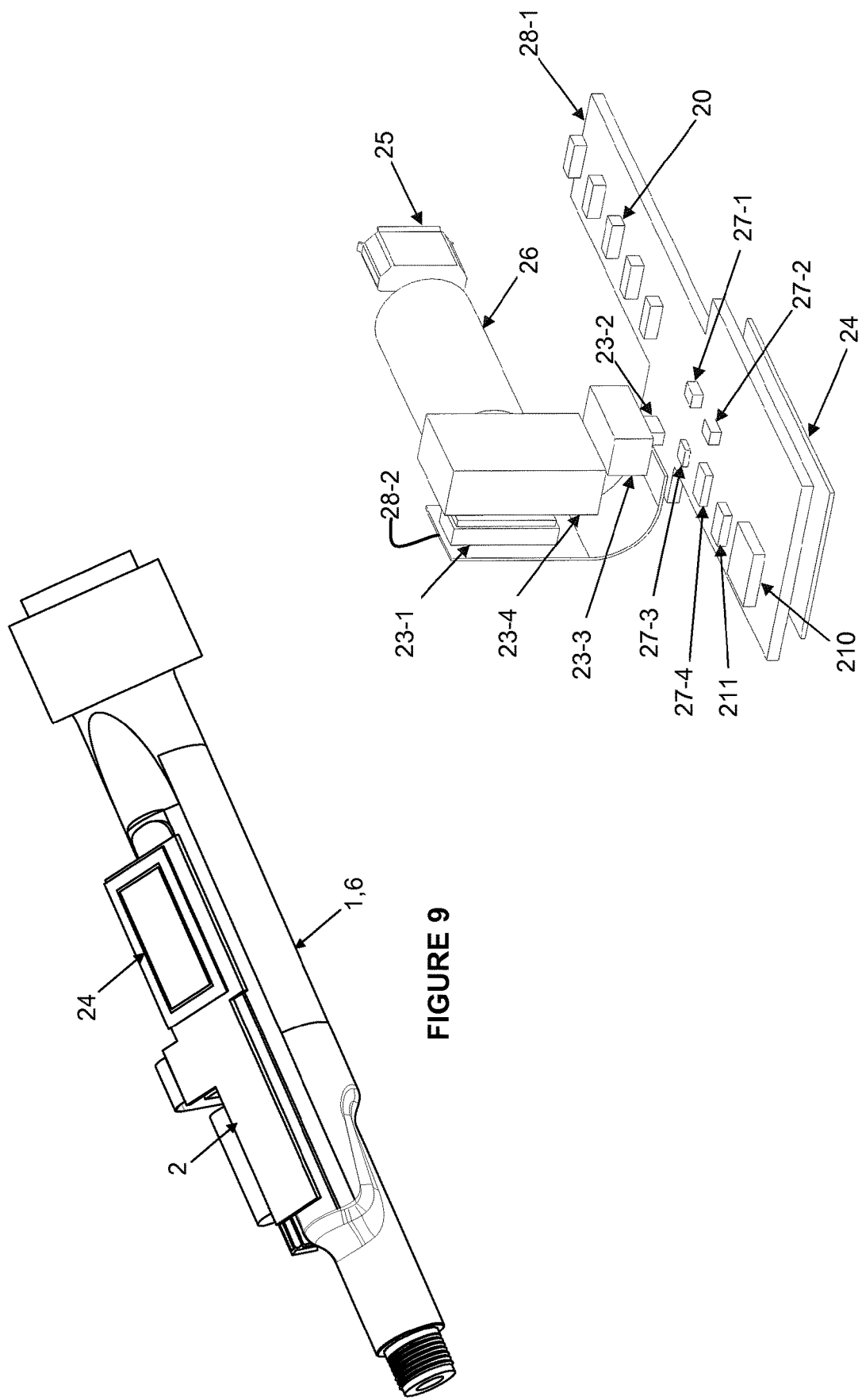

DRUG DELIVERY DEVICE WITH REMOVABLY ATTACHABLE SENSOR DEVICE

CROSS REFERENCE TO RELATED APPLICATIONS

The present application is the national stage entry of International Patent Application No. PCT/EP2016/080500, filed on Dec. 9, 2016, and claims priority to Application No. EP 15199192.4, filed in on Dec. 10, 2015, the disclosures of which are incorporated herein by reference.

TECHNICAL FIELD

The disclosure relates to a drug delivery device with a removably attachable sensor device, which is for instance removably attachable to a drug delivery device such as an injection pen.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning (dialing) a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose.

It has been described, for instance in WO 2011/117212, to provide a supplementary device comprising a mating unit for releasably attaching the device to an injection/drug delivery device. The device includes a camera and is configured to perform optical character recognition (OCR) on captured images visible through a dosage window of the injection pen, thereby to determine a dose of medicament that has been dialed into the injection device. In order for such a supplementary device to successfully determine the dose, the dosage window must remain stationary. However not all drug delivery devices operate in this way.

Furthermore it may be desirable that the supplementary device enables manual reading of dose information, e.g. through a dose indicating window of the drug delivery device. The supplementary device should therefore not obstruct a dose indicating window on the outer surface of a housing of the drug delivery device. It is also known to provide encoded information, e.g. on a number sleeve of a drug delivery device, which encoded information is recognizable by the supplementary device attached to the drug delivery device. Since the encoded information is located on a moveable element of the drug delivery device the size of the code may limit the precision of code detection. In typical situations only a specific portion of the code is readable by the supplementary device or sensor device. For providing a high degree of accuracy a rather high density of code information must be provided on a moveable element of the drug delivery device. Reducing the geometric size of the code and the code information might be detrimental to the reading or sensing performance of the sensor device or of the supplementary device. Enlarging of the code or code information, e.g. on the outer surface or outer circumference of a number sleeve is often not possible since the available space on the outer surface of a number sleeve is rather limited.

It is therefore an object of one aspect of the disclosure to provide a drug delivery device and a corresponding sensor device, hence a drug delivery system comprising a drug delivery device and a sensor device that enable detection and reading of encoded information on a moveable element of the drug delivery device with high precision and without increasing the size of the moveable element. It is a further aim to optimize the available space on the outer circumference of a moveable element, hence of a number sleeve of a drug delivery device.

SUMMARY

According to a first aspect a drug delivery device for setting and for injecting of a dose of an injectable medicament is provided. The drug delivery device comprises an elongated housing that extends along a longitudinal axis. The longitudinal axis defines an axial direction. The elongated housing extending in axial direction has a sidewall with at least a first aperture. The aperture may comprise a transparent window or may be provided as a cut-out in the sidewall of the elongated housing. The drug delivery device comprises at least one number sleeve that is rotatably supported inside the housing. The number sleeve comprises an outer surface. During setting of a dose of a medicament the number sleeve is rotatable in a dose incrementing direction. During dispensing of a dose the number sleeve is rotatable in a dose decrementing direction to return into its initial zero dose configuration. A first portion of the outer surface of the number sleeve is visible through the first aperture. The number sleeve comprises a non-visible code in the region of the first portion. Consequently, the non-visible code is unobstructed and visibly accessible through the first aperture. As the number sleeve is rotated, e.g. during dose setting a sequence of non-visible code fragments passes by the first aperture.

By providing a non-visible code in the region of the first portion the size of the non-visible code can be comparatively large. The non-visible code may overlap with visible information provided on the outer surface of the number sleeve. Making use of a non-visible code is therefore an effective means for saving space and for increasing the encoded information density on the outer surface of the number sleeve. The non-visible code is not visible by the human eye. However and when making use of an appropriate reading device the non-visible code is exclusively detectable and readable by such a reading device, e.g. by a sensing arrangement of a sensor device or supplementary device removably attachable to the drug delivery device.

In a typical application scenario the first aperture is completely covered by a sensing arrangement of the sensor device when attached to the drug delivery device. Hence, the first aperture is not visible to a user of the device when making use of the sensor device or supplementary device.

In this way, the total size of the non-visible code can be enlarged to a suitable extent so as to provide a sufficiently precise reading of the non-visible code.

The non-visible code comprises a code or code pattern provided on the outer surface of the number sleeve. The non-visible code may comprise an optical code. It may comprise a one- or two-dimensional code pattern, which is present on the outer surface of the number sleeve but which is invisible for a person under ordinary circumstances, i.e. when illuminated with electromagnetic radiation in the visible spectral range.

According to one embodiment the non-visible code is reflective and/or absorptive in non-visible spectral ranges of electromagnetic radiation. In this way the non-visible code is invisible to the human eye. It is exclusively readable by a sensing arrangement that operates in a spectral range of electromagnetic radiation outside the visible spectral range. Hence, the non-visible code and the sensing arrangement of the sensor device are configured to operate outside a spectral range that ranges from 380 nm to 680 nm. Typically, the non-visible code is reflective either in the UV spectral range, i.e. below 380 nm, below 350 nm or even below 300 nm or the non-visible code is reflective in the infrared spectral range, i.e. at wavelength above 680 nm, above 720 nm or above 790 nm. In this way, the non-visible code is invisible to the human eye.

Implementing a UV reflective code is of particular benefit since the comparatively low wavelength is particularly suitable for high resolution imaging. Moreover, UV light for reading of the non-visible code will not come along with a thermal heating of the outer surface and hence of the number sleeve of the drug delivery device. This may be beneficial for such medicaments that are heat sensitive.

The non-visible code is printed or coated on the outer surface of the number sleeve by way of a luminescent paint or luminescent ink that exhibits a well-defined luminescent response in a desired spectral range that is outside the visual spectral range. The luminescent paint, ink or the luminescent coating may be fluorescent or phosphorescent.

According to another embodiment the non-visible code comprises a reflective microstructure on the outer surface of the number sleeve. The reflective microstructure may be a reflective zero-order diffractive microstructure. The microstructure may comprise various steps or gaps. The microstructure further exhibits a desired reflectance in the non-visible range of electromagnetic radiation so that due to reflection of respective electromagnetic waves a diffraction pattern will arise that is indicative of the non-visible code in the region of the first portion on the outer surface of the number sleeve. It is particularly conceivable, that the reflective zero-order diffractive microstructure provides a kind of a holographic image when exposed to electromagnetic radiation of a desired wavelength, e.g. when subject to UV or infrared radiation.

The diffractive and reflective microstructure may be rather compact. An image creatable by the zero-order diffractive microstructure may be much larger than the microstructure itself. In this way, the reflective microstructure may inherently come along with a magnification effect.

According to another embodiment the at least first portion of the outer surface is metalized or comprises a metal coating. A metalized outer surface or a respective metal coating may be provided with the reflective microstructure. It is even conceivable, that the reflective microstructure is provided on a flexible foil that may be attached to the outer surface of the number sleeve. The flexible foil, the metalized outer surface or the metal coating thereof may be considered as a kind of a holographic label providing non-visible code for a given range of electromagnetic radiation. The reflective microstructure may comprise diffractive optical variable image device (DOVID) or may behave like a DOVID.

According to another embodiment the outer surface of the number sleeve comprises a second portion with numerous visible symbols extending along a helical pattern. The visible symbols may represent a sequence of increasing or decreasing numbers, wherein each number is representative for a particular dose size in accordance to a standardized unit system. If the drug delivery device is for instance configured for the injection of a medicament such like insulin, the visible symbols in the second portion of the outer surface may represent international units (IU). The second portion extending along a helical pattern may comprise visible symbols, such like 0, 2, 4, ... up to 100 or even up to 120. The helical pattern of the visible symbols of the second portion may comprise numerous revolutions around the outer circumference of the number sleeve. The visible symbols, hence the dose numbers are typically printed on the outer surface. They are readable and viewable through a second aperture or window of the elongated housing.

There are different configurations conceivable for the relative movement of number sleeve and elongated housing. It is conceivable that the number sleeve is rotatable along a helical path with regard to the elongated housing. Then, the second aperture or window will be located at a fixed position on the outer surface of the sidewall of the elongated housing. As the number sleeve is subject to a helical rotation a sequence or increasing or decreasing numbers will show up in the second aperture or window of the elongated housing. In other configurations it is conceivable, that the number sleeve is axially fixed inside the elongated housing. Then there will be provided a moveable element with the second aperture that moves along the second portion along the longitudinal axis, thereby visualizing only one or a few of the visible symbols at a time.

According to another embodiment the first portion and the second portion of the outer surface of the number sleeve overlap at least in sections. In this way, the non-visible code that coincides with or entirely fills the first portion overlaps at least a section of the visible symbols that coincide with or entirely fill the second portion on the outer surface of the number sleeve. The at least partial overlap of the first portion and the second portion, hence the overlap of the non-visible code with the visible symbols is beneficial in order to increase the information density on the outer surface of the number sleeve. Furthermore, the non-visible code may be provided with an increased size. In particular, the axial elongation of the non-visible code may be larger than the axial extension of a single visible symbol. Since the visible symbols are reflective in the visible spectral range and since the non-visible code is exclusively reflective in a non-visible spectral range a mutual overlap of visible symbols and non-visible code is generally conceivable.

It is of particular benefit, when the paint, the ink or the coating that provides the non-visible code is substantially transparent for electromagnetic radiation in the visible spectral range. Alternatively or additionally it is also conceivable, that the visible symbols are printed or coated in the second portion on the outer surface of the number sleeve with a paint, an ink or a coating that is substantially transparent in the UV spectral range and/or in the IR spectral range. Printing or applying the non-visible code on top of the visible symbols or vice versa applying the visible symbols above the non-visible code will then not lead to an obstruction of the code or symbols that are located beneath.

According to a further embodiment the non-visible code is located on top of at least one or several of the visible symbols or wherein at least one or several of the visible symbols are located on top of the non-visible code. In situations or configurations wherein the non-visible code is located on top of one or several of the visible symbols the non-visible code is typically transparent to electromagnetic radiation in the visible spectral range. In another scenario, wherein at least one or several of the visible symbols are located on top of the non-visible code the visible symbols are made of a visible material, e.g. a particular paint or ink that is substantially transparent for electromagnetic radiation in the UV spectral range and/or in the IR spectral range.

In this way the surface portion on the outer surface of the number sleeve that can be used for the non-visible code can be enlarged to such an extent that is beneficial for a precise and reliable automatic sensing and reading of the non-visible code without obstructing or deteriorating the visibility of the visible symbols on the outer surface of the number sleeve.

According to another embodiment the non-visible code is a two-dimensional code having a code array with numerous code lines and code columns. One of the code lines and the code columns extends in axial direction and wherein the other one of the code lines and the code columns extends in a tangential direction on the outer surface of the number sleeve, which is typically cylindrically-shaped. So the two-dimensional non-visible or invisible code is of cylindrical geometry and aligns parallel to the cylindrical shape of the number sleeve. It is generally conceivable, that the two-dimensional non-visible code is aligned parallel to the cylindrical shape or contour of the number sleeve whereas the visible symbols in the second portion are arranged along a helical pattern. The visible code may comprise a Hamming code, a de Bruijn sequence and/or a Manchester coding. A Manchester coding splits each de Bruijn sequence in two separate sequences, so that a processor or the sensing arrangement would recognize the transition between different bits of code rather than recognizing different bits of code as such.

The two-dimensional non-visible code may comprise a discrete code, hence a binary code, where the code pattern changes instantly for each increment. The two-dimensional code may also comprise a grayscale code, that changes floatingly from one gray value to another. When implemented as a discrete binary code, values of 0 or 1 are detected based on the intensity of the spatial light distribution that is reflected by the code and that reaches a sensing arrangement, typically comprising an optical detector with a respective decoder.

According to another embodiment the size of the first aperture of the housing through which at least a portion of the non-visible code is viewable or readable is at least as large as the height of a code column of the two-dimensional code. Typically, the size of the first aperture in tangential direction is even larger than or equal to the tangential extension of two adjacently located code lines. In this way a visual field of a sensing arrangement of the sensor device may contain always a complete code line or a complete code column.

By having a tangential size larger than or equal to the tangential extension of two adjacently located code lines even two code lines may appear simultaneously in the first aperture. As the number sleeve is dialed further, one of the two code lines will disappear at the benefit of a third code line appearing then in the first aperture. Typically, the first aperture comprises an axial extension larger than a tangential extension. The first aperture typically comprises an axial extension that is substantially equal to the axial length of a code line. A code line may be twice, four times, six times, or even ten times as large as the tangential extension of the code line, hence the height of a code field of a code line.

The rather rectangularly-shaped first aperture is of particular benefit for capturing and sensing the optical reflection of the non-visible code at a time. This enables a precise sensing and reading of the non-visible code information.

According to another embodiment the drug delivery device further comprises a movable element, typically configured as a gauge element which is movable along an axial path parallel to the longitudinal axis. The gauge element comprises the second aperture in form of a gauge window through which the outer surface of the number sleeve is visible. The gauge window is located beneath a third aperture in the sidewall of the housing. The third aperture in the sidewall of the housing typically extends in longitudinal or axial direction so that the gauge window of the gauge element is permanently located inside the third aperture.

Typically, the gauge element is purely axially slidably displaceable relative to the housing of the drug delivery device. The gauge element is rotationally locked to the housing of the drug delivery device and cannot be rotated with regard to the longitudinal axis as a rotation axis. In operation the gauge element covers that portion of the outer surface of the number sleeve that is located beneath the second aperture of the housing. In this way the number sleeve is effectively covered by the non-transparent gauge element except for that portion of the number sleeve that is visible through both, the third aperture in the sidewall of the housing and through second aperture, hence through the gauge window.

As a dose is for instance set the number sleeve is exclusively subject to a rotation relative to the housing whereas the gauge element is exclusively subject to an axial displacement relative to the housing. The axial movement of the gauge element corresponds with the rotational movement of the number sleeve and with the pitch of the helical pattern of the visible symbols of the second portion of the outer surface of the number sleeve. In this way, a sequence of increasing numbers will show up in the axially sliding gauge window as the number sleeve is subject to a dose incrementing rotation during setting of a dose.

According to another embodiment the number sleeve is axially fixed inside the housing and the number sleeve located radially inside the gauge element. In other words, the gauge element at least covers a portion of the number sleeve. The gauge element is located radially between the outer surface of the number sleeve and an inner surface of the housing. Furthermore, the number sleeve is threadedly engaged with the gauge element. It is due to the threaded engagement of number sleeve and gauge element that the gauge element is subject to a longitudinal or axial sliding motion as the number sleeve is rotated inside the housing. The gauge element is further in axial slidable engagement with the housing. For this the gauge element and the housing comprise at least one pair of radially extending protrusion engaging with a longitudinally extending groove by way of which a kind of a splined engagement is provided between the gauge element and the housing. In this way the gauge element is prevented from rotating relative to the housing.

In another embodiment the gauge element comprises at least one detectable indicator at a predetermined axial location. The total information content provided by the non-visible code may not be sufficient to encode all settable dose sizes of the drug delivery device. It is conceivable, that the non-visible code comprises only four or five bits that are not sufficient to encode all numbers between 0 and e.g. 120. During setting of a dose it is hence conceivable, that the number sleeve is subject to numerous revolutions. Since the number sleeve is axially fixed inside the housing its non-visible code will repeatedly show up in the first aperture.

In order to provide an absolute and unequivocal determination of a dose size the gauge element is provided with at least one detectable indicator at a predetermined axial location. Since the gauge element is subject to an axial displacement also the detectable indicator will be moved in axial direction as a dose is dialed. A sensor device removably attachable to the drug delivery device typically comprises a sensing arrangement to at least roughly detect the axial position of the detectable indicator of the gauge element. In this way the sensing arrangement may precisely distinguish between various revolutions of the number sleeve inside the housing.

In another aspect the disclosure also relates to a sensor device that is removably attachable to the drug delivery device as described above. The sensor device comprises a sensing arrangement overlying the first aperture when the sensor device is attached to the drug delivery device. The sensing arrangement is configured to receive optical signals from the non-visible code as the non-visible code is viewable through the first aperture. The sensor device further comprises a circuitry that is connected to the sensing arrangement. The circuitry is configured to process signals obtained from the sensing arrangement when the sensing arrangement receives optical signals.

The sensing arrangement is further configured to read a portion of the non-visible code through the first aperture and the circuitry is further configured to determine, based on the externally visible portion of the non-visible code, the angular position of the number sleeve relative to the housing. From this the circuitry is configured to derive information relating to a drug dose to which the drug delivery device is currently dialed.

The sensing arrangement typically comprises at least a light source and an optical detector that are operable in a non-visible spectral range. The light source and the detector may operate in the UV spectral range or in the IR spectral range. The optical detector typically comprises an array of numerous light sensitive pixels in order to capture a two-dimensional image of the non-visible code that is viewable through the first aperture of the housing of the drug delivery device.

According to another embodiment the sensor device comprises an array of sensors that are arranged within the sensor device and that are separated in the longitudinal or axial direction. The sensors are configured to detect the axial position of the detectable indicator of the gauge element. The sensors or the array of sensors may be implemented as optical sensors. However, the sensors may be also implemented as capacitive or inductive sensors so as to be capable to detect the axial position of the detectable indicator of the gauge element.

In a further aspect there is also provided a drug delivery system comprising a drug delivery device as described above and further comprising a sensor device or supplementary device removably attachable to the drug delivery device at least for reading and/or tracking of a dose size information.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39), des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure as it is defined by the claims. Further, it is to be noted, that any reference numerals used in the appended claims are not to be construed as limiting the scope of the disclosure.

BRIEF DESCRIPTION OF THE FIGURES

In the following, an embodiment of the display arrangement, the drive mechanism and the drug delivery device is described in detail by making reference to the drawings, in which:

FIGS. 2A to 2D are illustrative simplified views of various components, and combinations of components, of a drug delivery device such as that of FIG. 1 with which a sensor device according to various embodiments may be used;

FIG. 6 E is a side view of the configuration according to FIG. 6D;

FIG. 8 shows an example of a physical arrangement of the components of the sensor device depicted in FIG. 7;

FIG. 9 shows the sensor device as depicted in FIG. 8 in situ on a drug delivery device;

DETAILED DESCRIPTION

Figure 1:
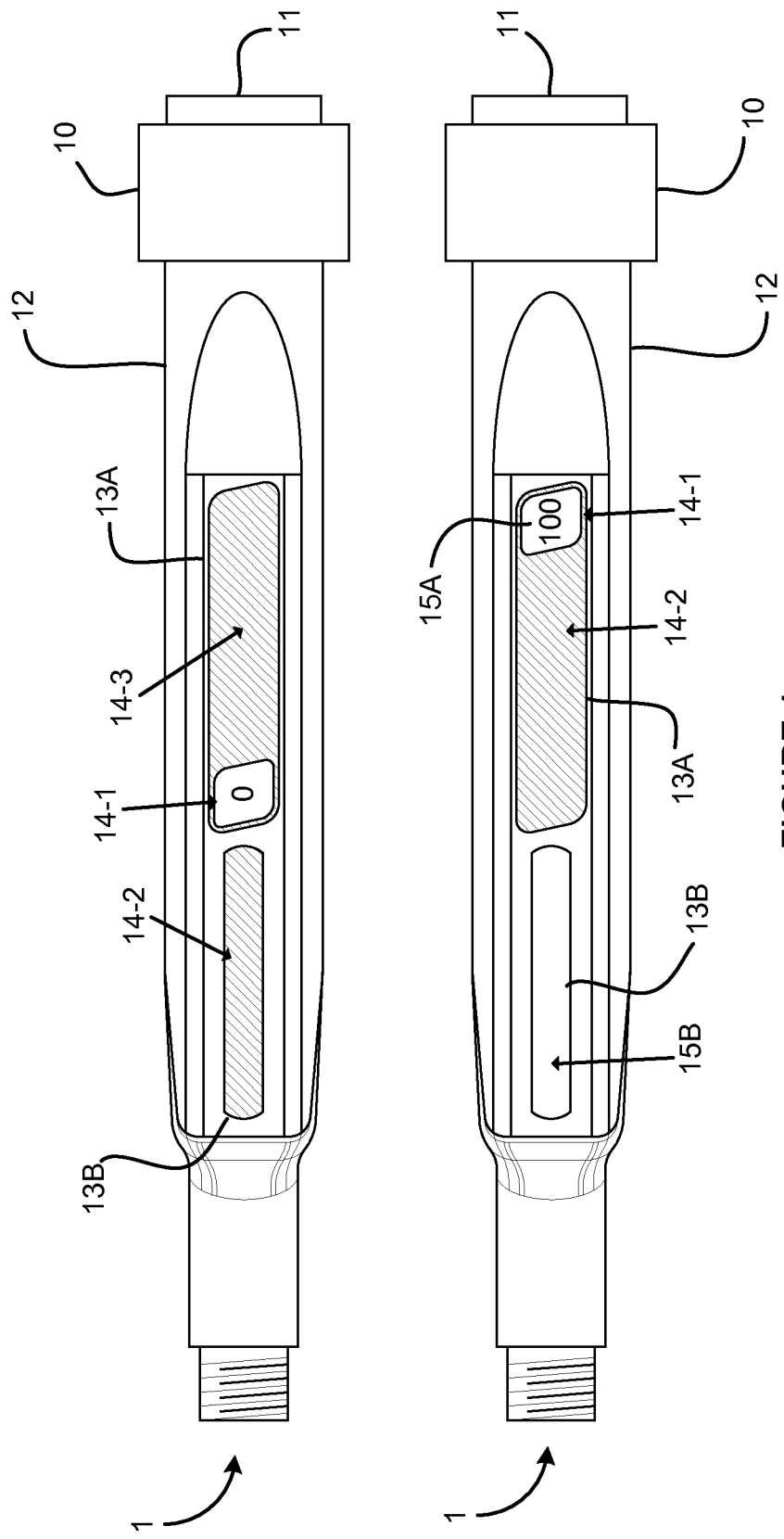
FIG. 1 shows two views of a drug delivery device 1 with which a sensor device according to various embodiments of the disclosure may be used.

In the description and drawings, like reference numerals refer to like elements throughout.

FIG. 1 shows two views of a drug delivery device 1, in this example an injection device, with which a sensor device (also referred to as a supplementary device—not shown) according to various embodiments of the disclosure may be used.

The drug delivery device 1 of FIG. 1 is configured such that a user is able to adjust the drug dosage (or number of drug doses) that is to be delivered (or dispensed) using the device 1. In the example of FIG. 1, this is achieved by rotating (or dialing) a dose selector 10 which causes an internal dialing mechanism (not shown) to adjust an amount of the drug that is to be dispensed once a drug delivery mechanism (not shown) is actuated. In this example, the drug delivery mechanism is actuated by pressing a button 11 on the device.

The drug delivery device 1 comprises an external housing 12 in which is formed at least one aperture or window 13A, 13B. As will be appreciated, an aperture may simply be a cut-away area of the external housing 12, whereas a window may be a transparent portion of the housing through which components of the device may be seen. For convenience, the at least one aperture or window 13A, 13B, will hereafter simply be referred to as the third aperture 13A and the fourth aperture 13B, respectively.

The third and fourth apertures 13A, 13B allow a movable gauge element 14 to be visible from the exterior of the housing 12. The drug delivery device 1 is configured such that as the dose selector 10 is dialed, the movable gauge element 14 is caused to be moved thereby to indicate a selected dose to the user. More specifically, as the dose selector 10 is dialed, the gauge element 14 moves axially along an underlying surface 15A, 15B thereby to indicate the selected dose. In the example of FIG. 1, a surface 15A underlying at least part of the gauge element 14 is located on the outer surface of a number sleeve 65. The underlying surface 15A and/or the underlying surface 15B may coincide with the outer surface 70 of the number sleeve 65.

Figure 10A:
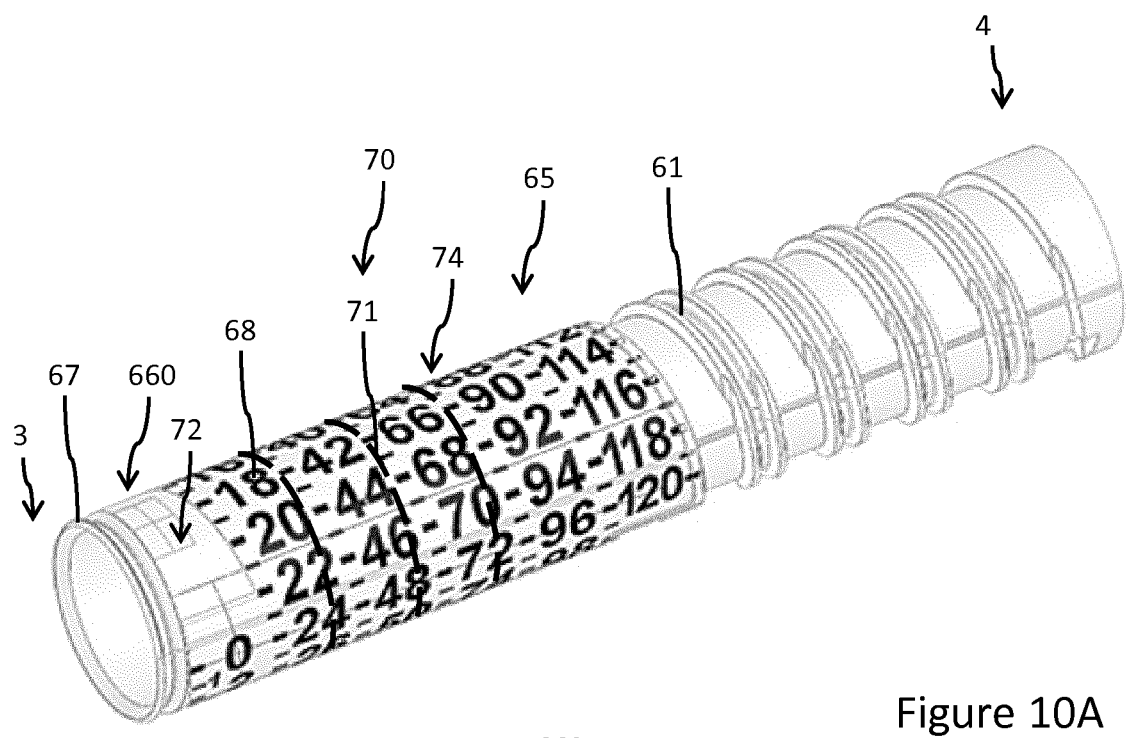
FIG. 10A is a perspective illustration of an isolated number sleeve.

The number sleeve 65 as shown in FIG. 10A has numbers 68 indicative of drug doses provided on its outer surface, with the number indicating the currently selected dose being visible through the third and fourth apertures 13A, 13B. In this example, the number sleeve 65 is visible through a gauge window or through a second aperture 14-1 formed in the movable gauge element 14. Other parts of the movable gauge element 14 are discussed below.

The uppermost view of the drug delivery device 1 shown in FIG. 1 illustrates the situation before any dialing has been performed. Consequently, the movable gauge element 14 is at its first (or initial) position at a first end of the path along which it is able to move. In this example, when the movable gauge element 14 is at the first end of its path, the portion of the number sleeve 65 that is visible through the gauge window or through the second aperture 14-1 shows the number zero (i.e. a zero dose).

The bottommost view of the drug delivery device 1 shown in FIG. 1 illustrates the situation after dialing has been performed. Consequently, the movable gauge element 14 has moved axially along the path that is visible through the third aperture 13A away from its first position. In this example, the device 1 has been dialed to its maximum dose and as such, the movable gauge element 14 has moved to the second end of its path. The maximum dose in this example is "100" and so the portion of the number sleeve 65 that is visible through the gauge window 14-1 shows the number "100".

The number sleeve 65 and the respective underlying surface 15A underlie and are visible through the third aperture 13A, whereas a further underlying element 15B underlies and is sometimes visible through the fourth aperture 13B. The further underlying surface 15B may or may not include any numbers. The further underlying surface 15B is visually distinguishable from a second part 14-2 of the movable gauge element 14 which overlies it and which is configured to move axially along it. For instance, the second part 14-2 of the movable gauge element 14 may be of a different reflectance to the further underlying surface 15B. For example, one of the gauge element 14 and the underlying surface 15B may be of a light colour (e.g. may be made of a light coloured polymer) and the other may be of dark colour (e.g. may be made of a dark coloured polymer).

The user may, therefore, be able to determine the selected dose by determining the proportion of the third aperture 13A in which the gauge element 14 (specifically, the second part 14-2) is visible compared to the proportion in which the further underlying surface 15B is visible. This can be seen from FIG. 1, in which, when the device 1 is dialed to its zero dose, the gauge element 14 covers the entire length of the path that is visible through the fourth aperture 13B. In contrast, when the device 1 is dialed to its maximum dose, none of the gauge element 14 is visible through the second window. Instead, the further underlying surface 15B is visible along the entire length of the path defined by the fourth aperture 13B.

The number sleeve 65 underlying the gauge element 14 is also visually distinguishable from the movable gauge element 14 which overlies it and which is configured to move axially along it. For instance, gauge element 14 may be of a different reflectance to the number sleeve 65. For example, one of the gauge element 14 and the underlying surface 15A may be of a light colour (e.g. may be made of a light coloured polymer) and the other may be of dark colour (e.g. may be made of a dark coloured polymer). In the examples shown in the Figures, the number sleeve 65 and underlying surface 15B are of a higher reflectance than the movable gauge element 14.

FIGS. 2A to 2D and FIG. 3 are simplified schematics of components of a drug delivery device such as that of FIG. 1. The purpose of FIGS. 2A to 2D is to illustrate the operation of a drug delivery device 1 such as that of FIG. 1; they are not intended to be accurate representations of the exact design of the components.

FIG. 2A is a simplified schematic of the number sleeve 65 with the underlying surface 15A, that coincides with the outer surface 70 on the outer circumference of the tubular sleeve 65. The sleeve 65 has numbers provided on its surface. In some examples, the numbers, ranging from the minimum dose to the maximum dose, may be provided helically around the surface of the number sleeve.

FIG. 2B is a simplified schematic of a movable gauge element 14. The gauge element 14 comprises a first section 14-4 in which the gauge window 14-1 is provided. In this example, the first section is 14-1 a collar which is configured to encircle the number sleeve 65 and its underlying surface 15A (as can be seen in FIGS. 2C and 2D). Extending in opposite directions from the first section 14-4 are the second part 14-2 and a third part 14-2. The second and third parts 14-2, 14-3 extend generally parallel to the longitudinal axis of the number sleeve 65.

The second part 14-2 of the movable gauge element is configured to extend from the first part 14-2 by a length sufficient to fill the entire second window 13B when the movable gauge is in its first position. The second part 14-2 may also serve to obscure a portion of the exterior surface of the number sleeve 65, when the gauge element moves away from its first position. The third part of the movable gauge element 15-3 is configured to obscure a portion of the exterior surface of the number sleeve 15A, when the gauge elements moves between its first and second positions. In this way, only the portion of the number sleeve that underlies the gauge window 14-1 is visible through the third aperture 13A of the device housing 12. The gauge window 14-1 represents a second aperture of the drug delivery device.

The rotational movement $NS_R$ of the number sleeve 65 and axial movement $G_E$ of the gauge element 14 are interdependent. Put another way, the dialing mechanism of the device 1 is configured such that when number sleeve 65 is caused to rotate, the gauge element 14 is caused to move or translate axially along its path. Moreover, the degree of rotation of the number sleeve 65 corresponds proportionally to the extent of axial movement of the gauge element 14.

Figure 3:
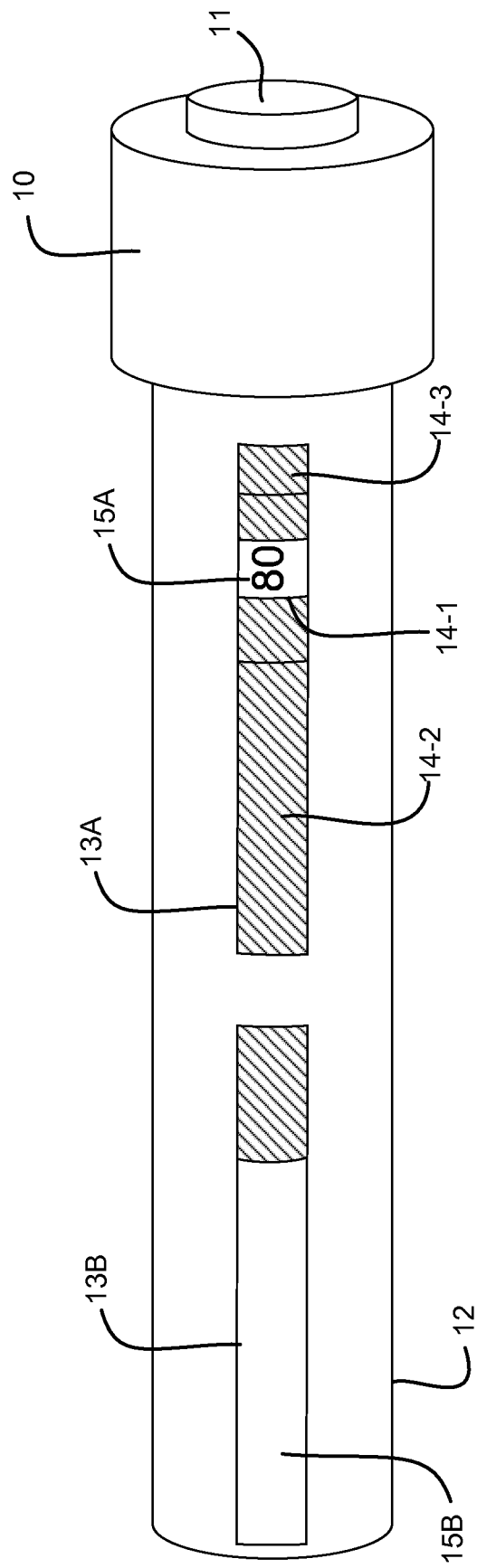
FIG. 3 shows another simplified view of the device when a dose has been dialed.

FIG. 2C shows the gauge element 14 in its initial position in which, in this example, it indicates a zero dose. FIG. 2D shows the number sleeve 65 and gauge element 14 following rotation of the number sleeve 65 and translation of the gauge element 14 from its first position. FIG. 3 shows this arrangement of FIG. 2D within a simplified version of the device housing 12.

Various dialing mechanisms for adjusting a dose to be delivered to a user which transform rotation of a dose selector 10 into rotational movement of a number sleeve 65 and axial movement of a gauge element 14 (as described above) are known in the art. Two such mechanisms are described in WO2013/110538A1 and WO2008/145171A1. As such mechanisms (and also drug delivery mechanisms which cause delivery of the drug once the dose has been dialed) are known in the art, they will not be described herein in any detail.

One specific but non-limiting example of the number sleeve 65 is given in the illustration according to FIG. 10A. The number sleeve 65 is of generally tubular shape. It comprises an outer surface 70. The outer surface 70 comprises a first portion 72 that is provided with a non-visible code 660. In the present illustration also shown in FIG. 6A the non-visible code 660 is exclusively provided in the first portion 72. The first portion 72 substantially coincides with the spatial extension of the non-visible code 660. It is only for illustration purpose, that the non-visible code 660 is made visible in the various Figures.

On the outer surface 70 there is further provided a second portion 74. In the second portion there are provided numerous visible symbols 68 that are arranged along a helical pattern 71 as it is apparent from FIGS. 6A and 10A. The first portion 72 and the second portion 74 may be substantially overlapping as illustrated in FIG. 6A. Hence, the non-visible code 660 may overlap at least a portion of the visible symbols 68 of the helical pattern 71. In this way, the size, in particular the axial size of the two-dimensional non-visible code 660 is extended to such a size that the code 660 is particularly suitable for a reliable and failure safe reading of the non-visible code information.

In the present embodiment the number sleeve 65 is axially fixed inside the housing 12 of the drug delivery device 2. Near a distal end 3 the number sleeve 65 comprises an annular groove 67 that engages with a correspondingly-shaped radially inwardly extending structure on the inner surface of the housing 12. It is free to rotate relative to the housing with regard to a central axis that extends parallel to the elongation of the number sleeve 65. Near a proximal end 4 the number sleeve 65 is provided with an outer thread 61 by way of which the number sleeve 65 is threadedly engaged with the gauge element 14. The gauge element 14 is hindered to rotate relative to the housing 12. It is hence rotatably fixed to the housing 12. Rotation of the number sleeve 65 is in some embodiments caused by rotation of the dose selector 10.

One of the gauge element 14 and the housing 12 may comprise a radial protrusion that engages with an axially extending groove of the other one of the gauge element 14 and the housing 12. In this way the gauge element 14 is slidably supported inside the housing 12 but is rotatably constrained to the housing 12. The gauge element 14 typically comprises an inner thread 61A that engages the outer thread 61 of the number sleeve 65. A rotation of the number sleeve 65 during dose setting or dose dispensing therefore leads to a translational and purely axial sliding motion of the gauge element 14.

When rotating the number sleeve 65 the visible symbols 68, hence the dose indicating numbers provided in the second portion 74 on the outer surface 70 of the number sleeve 65 show up in the third aperture 13A and in the second aperture 14-1 as the gauge element 14 travels in axial direction relative to the housing 12.

Figure 10B:
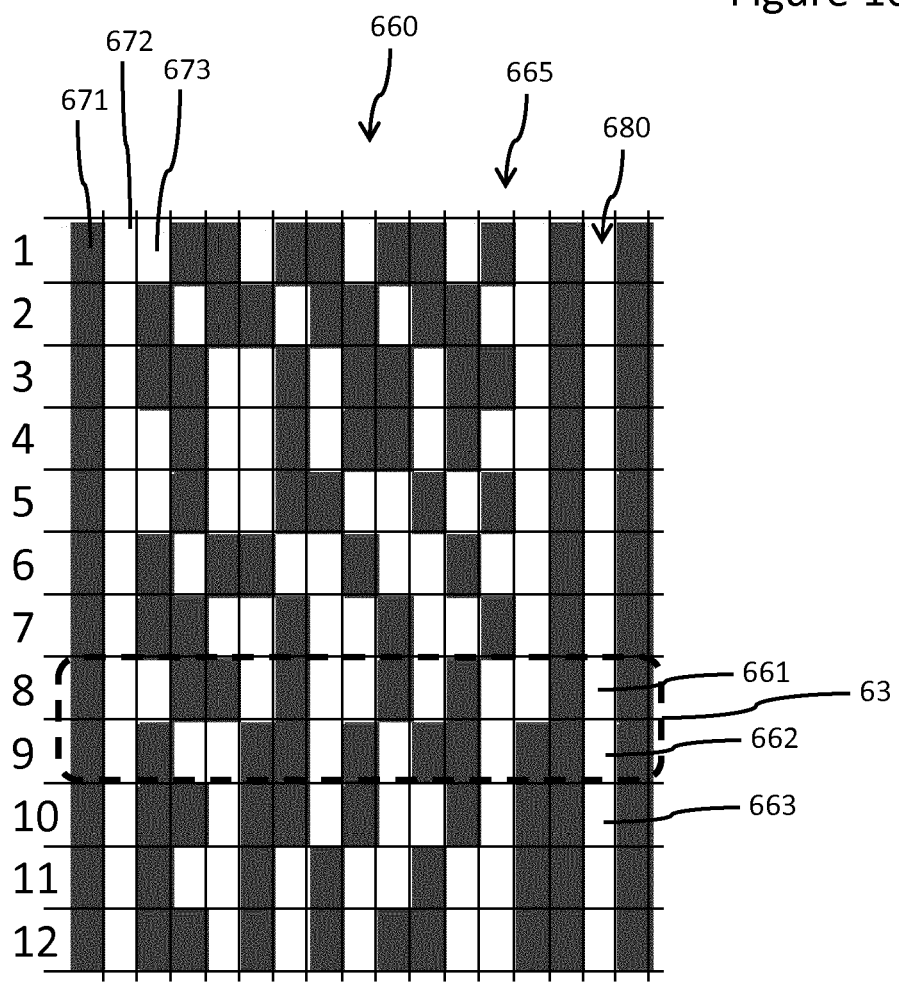
FIG. 10B is an example of a two-dimensional non-visible code on the outer circumference of the number sleeve in comparison to the location of the first aperture.
Figure 10C:
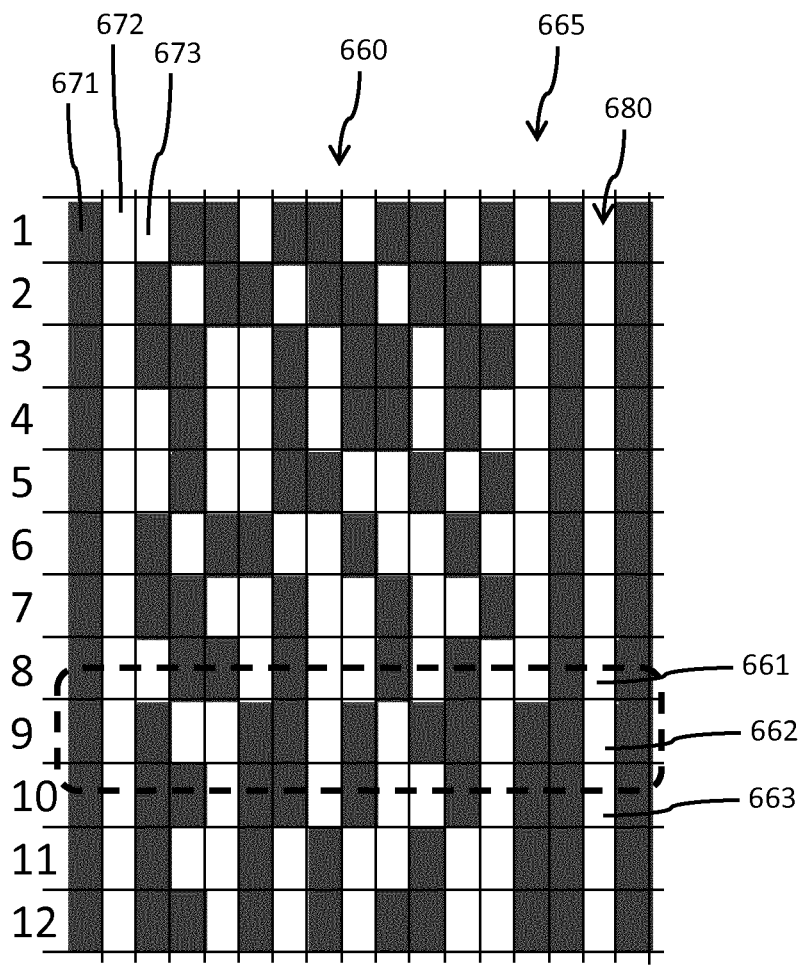
FIG. 10C is another illustration of the code according to FIG. 10B in a different position relative to the first aperture compared to the configuration according to FIG. 10B

The non-visible code 660 of the first portion 72 of the outer surface 70 of the number sleeve 65 is exemplary illustrated in FIGS. 10B and 10C. There are illustrated 12 code lines and 18 code columns that form an array 665 of a binary code. Some code lines are exemplary denoted as code lines 661, 662 and 663 and some columns are denoted as 671, 672, 673.

The housing 12 of the drug delivery device 1 includes a first aperture 63 through which a portion of the number sleeve 65, on which part of the code 660 is provided, is visible. The further window 63 is positioned and oriented relative to the number sleeve 65 such that a portion of the code is externally visible through the further window 63 regardless of the rotational orientation of the number sleeve 65. The first aperture 63 is positioned and oriented relative to the number sleeve 65 such that, as the number sleeve 65 rotates through a single complete rotation, different sections of the code 660 will be visible at each rotational orientation. The further aperture is, in this example, provided on a different side of the device housing 12 (or, if the housing is cylindrical or otherwise rounded, around the exterior surface of the device housing 12) from the at least one window 13A, 13B through which the movable gauge element 14 is visible. In this way, the movable gauge element 14 does not obstruct the code 660 from view.

Figure 7:
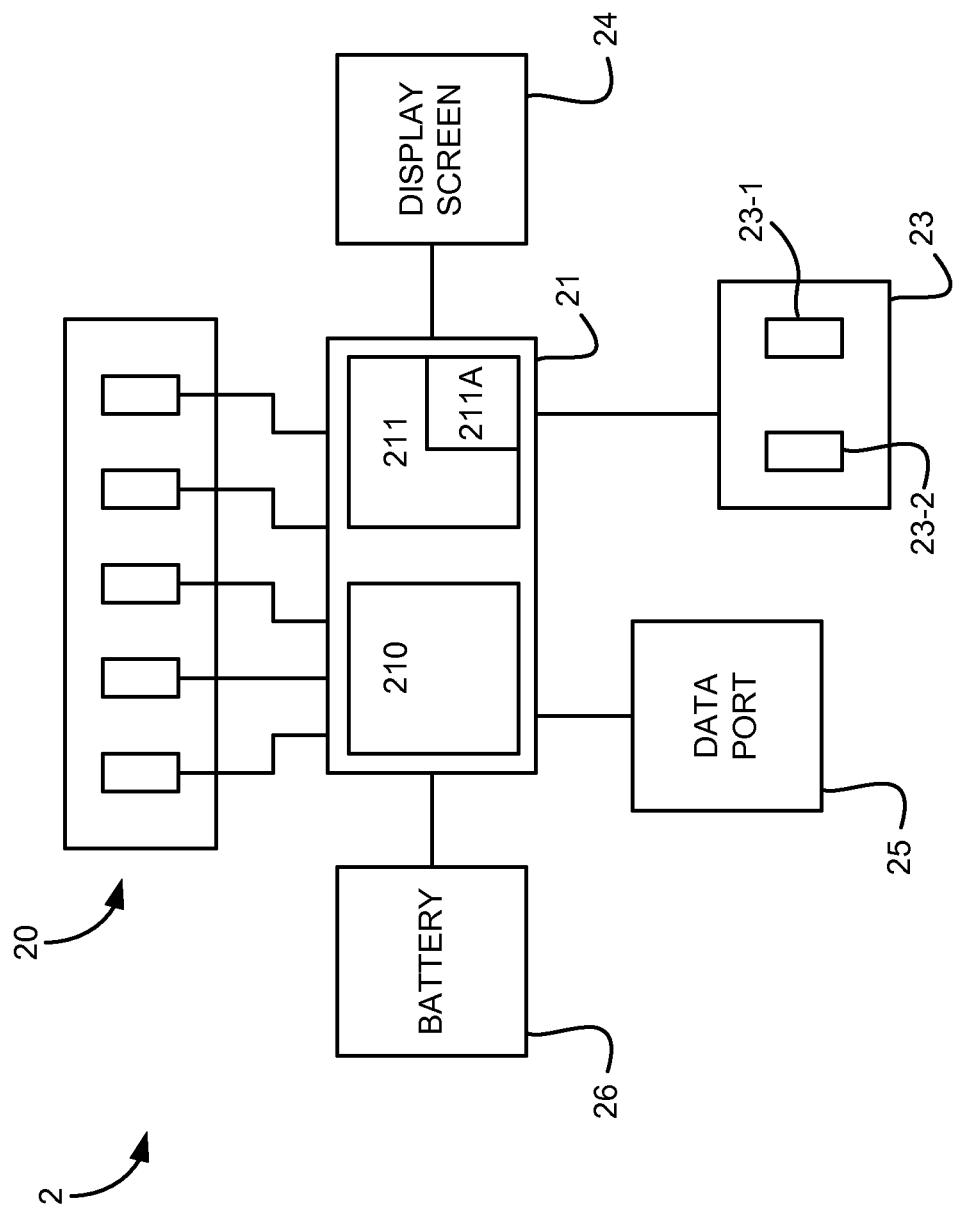
FIG. 7 is a simplified block diagram of a sensor device according to embodiments of the disclosure.

As shown schematically in FIG. 7, the sensor device 2 comprises a circuitry 21 with a sensing arrangement 23. The sensing arrangement 23 is arranged within the sensor device 2 such that, when the sensor device 2 is attached to the drug delivery device 6, the sensing arrangement 23 is operable to read the non-visible code 660 that is externally visible on the drug delivery device 6 through a first aperture 63 in the housing 12. In this example, at least part of the encoded information 660 is visible through the first aperture 63. In some other examples, such as are discussed below, at least part of the encoded information may be provided on a portion of the exterior of the housing 12 which underlies the sensing arrangement 23.

The sensing arrangement 23 may be of any suitable type as long as it enables the encoded information 660 to be read. For instance, the sensing arrangement may be an optical sensing arrangement comprising a camera.

The size of the first aperture 63 is illustrated in FIGS. 10B and 10C in a dashed rectangle. The size of the first aperture 63 is configured to provide visualization of an entire code line 661, 662, 663. In this way and due to the overlapping arrangement of the non-visible code 660 with the visible symbols 68 the axial size of the non-visible code 660 can be enlarged to an extent that provides unequivocal and highly reliable code reading. The code lines 661, 662, 663 are aligned in axial direction whereas the code columns 371, 672, 673 extend in tangential direction, hence along the outer circumference of the tubular-shaped outer surface 70 of the number sleeve 65.

The height of the code columns will equal 360 degrees divided by 12, hence the height of each code line may equal about 30 degrees. In the presently illustrated embodiment the tangential width, hence the vertical size of the first aperture 63 is at least equal to or larger than the size of two adjacently arranged code lines 661, 662. Hence, the total size of the first aperture in tangential direction may be about 60 degrees. The present size of the first aperture 63 in tangential direction is beneficial in that always at least one complete code line 661 will be readable through the first aperture. In the configuration according to FIG. 10B two entire code lines 661, 662 are visible through the first aperture 63.

Taking into account some tolerances of the imaging of the code 660 or tolerance of the angular position of the number sleeve of about +/−0.30 units the tangential size of the first aperture may be increased to about 70°. With an appropriate sensing arrangement 23 the reading of the code 660 may be conducted even without the start-sections, end sections or 'quiet' sections of the code. Then the tangential size of the first aperture 63 may be reduced to about 60° even including the above mentioned tolerance margins.

The sensing arrangement of the sensor device is particularly configured to analyze the captured code lines 661, 662. Moreover, the code sequence may be stored in the circuitry, in particular in a memory 221. The circuitry may be provided with a threshold function to decide which one of the two consecutive code lines 661, 662 is dominantly present in the first aperture 63. It may be only for an infinitesimally small angular range that the circuitry will not be able to decide which one of the code lines 661, 662 is dominantly present inside the first aperture 63. For this it is of particular benefit, when the tangential size of the first aperture does not exceed but exactly matches with the twofold tangential size of a code line 661 or 662.

As soon as the number sleeve 65 is dialed further from the configuration according to FIG. 10B a configuration according to FIG. 10C may arise. There, only the code line 662 is completely visible through the first aperture 63 whereas a tangentially preceding and a proceeding code line 661 or 663 are only visible partially. Depending on the spatial resolution and the pattern recognition of the sensing arrangement and the circuitry 21 the sensor device 2 is capable to determine that the number sleeve 65 has been dialed one increment further.

With the illustrated 12 code lines at least 12 consecutive dose sizes can be encoded on the outer circumference and on the outer surface 70 of the number sleeve. However, for encoding a total number of for instance 120 units with an increment of only 1 unit ten revolutions of the number sleeve 65 would have to be implemented.

In order to reduce the number of revolutions of the number sleeve it is even conceivable, that 24 different angular positions can be encoded with the 12 code lines. In the present embodiment, each code line may represent an even number of dose units, such like (0, 2, 4, 6, . . . , 22). If the sensing arrangement detects a configuration according to FIG. 10 with one completely viewable code line 662 and two additional but only partially viewable code lines 661, 663 the circuitry 21 may recognize such a scenario that the number sleeve is now rotated to an odd dose number (1, 3, 5, 7, 9, . . . , 23). Dialing the number sleeve 65 further for half a code line 661 two entire code lines 662, 663 will show up in the first aperture 63. Both of these scenarios may be well distinguished by the circuitry 21.

The code 660 may comprise a Hamming Code, wherein some portions of the code 660 are redundant code fragments. For representing 24 angular positions 5 bits of codes are substantially sufficient. Some columns of the code 660 are used as a start bit or as a stop bit in order to provide a well-defined starting point for the code information. By means of redundant code fragments the security and unequivocal readability o the code 660 can be enhanced.

When implemented as a de Bruijn sequence the code may be for instance represented by a sequence of code portions extending all along the helical pattern 71 of the visible symbols. Hence, the first portion 72 of the number sleeve 65 and the second portion 74 of the number sleeve with non-visible code and with visible symbols substantially overlap.

Simultaneously to an axial tracking of the gauge element 14 the sensing arrangement 23 overlying the first aperture 63 generates electromagnetic radiation in a non-visible spectral range by means of a light source 23-2. The electromagnetic radiation, typically UV or IR radiation is directed towards the first aperture 63. Non-visible electromagnetic radiation reflected from the non-visible code 660 is reflected towards a detector 23-1 of the sensor device 2. Signals of the detector 23-1 and hence of the sensing arrangement are processed by the circuitry 21 in order to track and to determine the actual angular position of the number sleeve 65.

Figure 6D:
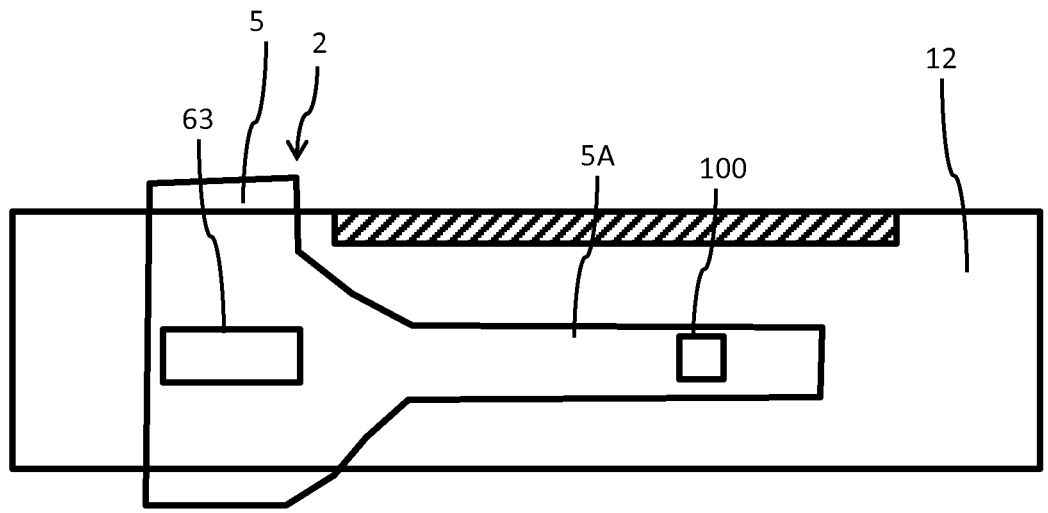
FIGS. 6A to 6C are illustrative simplified views of the number sleeve and its arrangement inside the elongated housing so that a portion thereof is viewable through the first aperture of the housing.
FIG. 6 D is a top view onto the drug delivery system where the sensor device is attached to the drug delivery device thereby covering the first aperture in the housing of the drug delivery device.
Figure 6E:
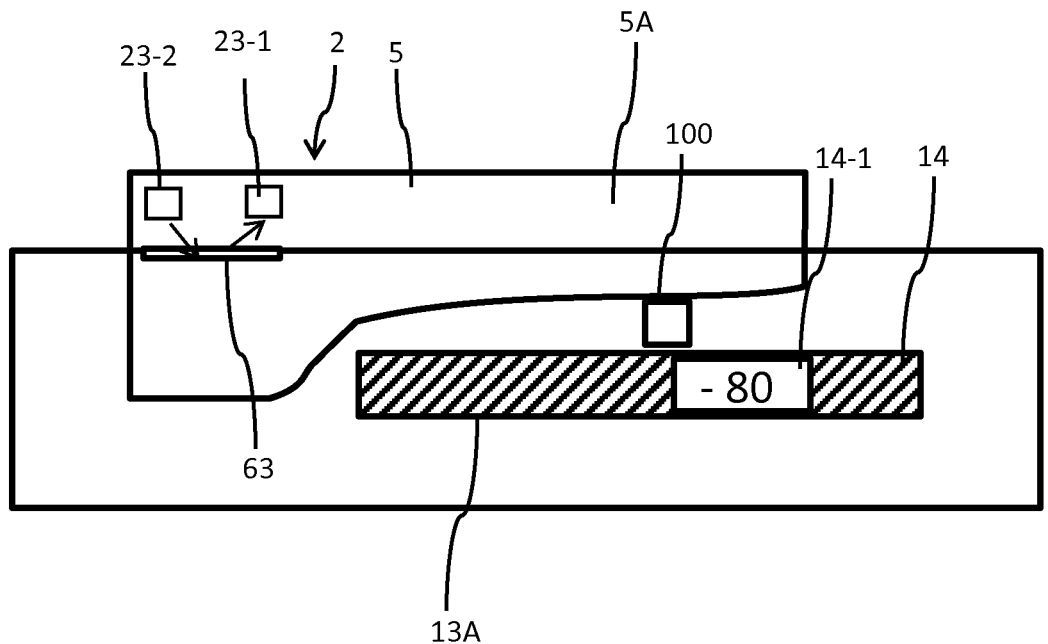

In the sketches of FIGS. 6D and 6E it is apparent, that the sensor device 2 comprises a body 5 by way of which the sensor device 2 is detachably fastened to the outer surface of the housing 12. The body 5 comprises an axially elongating protruding portion 5A. In this protruding portion 5A an array 20 of axial sensors 20-1, 20-2, 20-3, 20-4, 20-5 may be positioned. The gauge element 14 which is provided with a detectable indicator 100 is subject to a well-defined and discrete movement in axial direction as the number sleeve 65 has been rotated a complete revolution.

Figure 5:
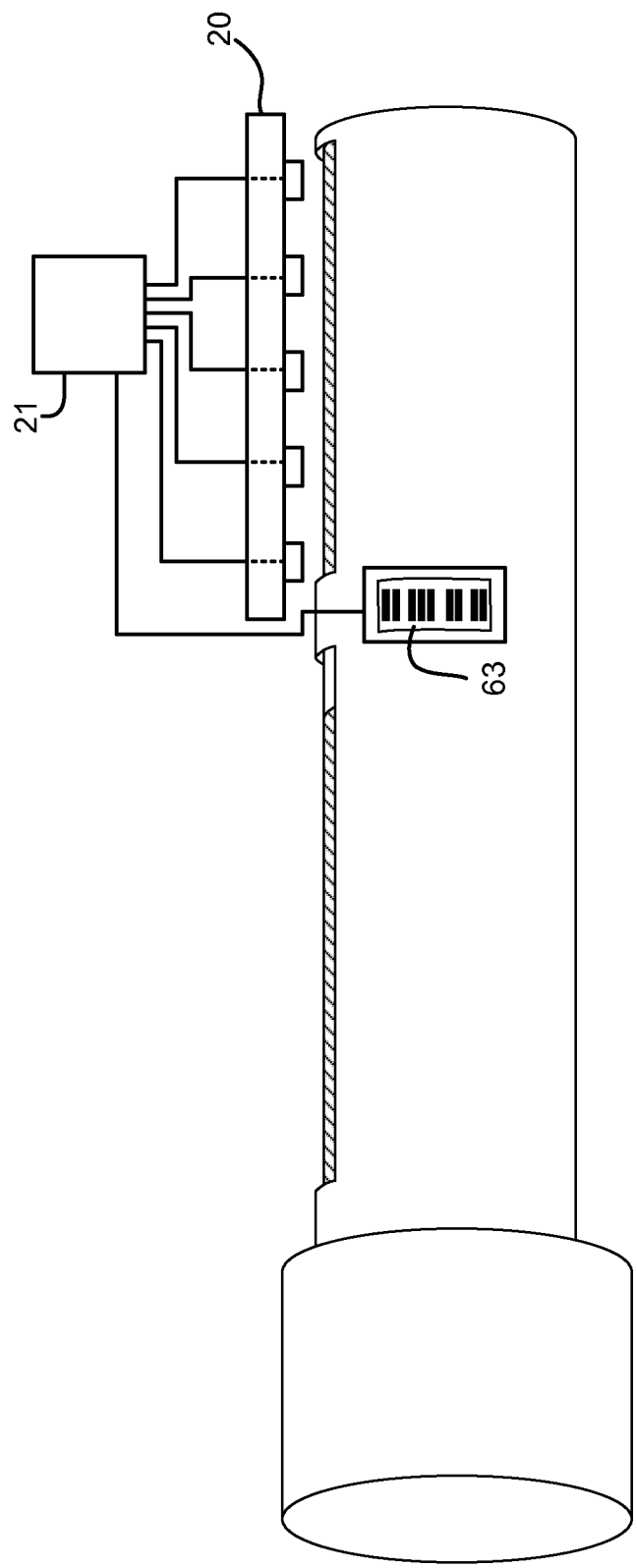
FIG. 5 shows a schematic side view of the drug delivery device with the circuitry and the sensing arrangement.

The circuitry 21 of the sensor device 2 of FIG. 5 is configured to determine, based on the encoded information 660, information relating to operation of the drug delivery device 1. In some specific examples, the circuitry 21 is configured to determine a current dose to which the device 1 is dialed, based on the encoded information 660 and the signals output from the sensors of the array 20. For instance, the signals output from the array 20 may be utilised by the circuitry 21 to determine the number of complete rotations of the number sleeve 65 that have occurred and the encoded information 660 read by the sensing arrangement 23 may be utilised to determine the rotational orientation of the number sleeve 65. Put another way, the signals output from the array 20 may be used to determine roughly the extent of axial translation of the moveable gauge element 14, with the encoded information 660 read by the sensing arrangement being used with the rough determination to more precisely determine the extent of rotation of the number sleeve and/or the translation of the movable gauge element 14 in order to determine the currently dialed dose.

The array 20 of sensors 20-1, 20-2, 20-3, 20-4, 20-5 is capable to detect the axial position of the detectable indicator 100 as a dose is dialed or set. The position of the detectable indicator 100 along the protruding portion 5A is hence indicative of the number of complete revolutions the number sleeve 65 has turned since the beginning of a dose incrementing rotation.

The sensors 20-1 to 20-5 may be implemented as optical sensors. They could be also implemented as magnetic, capacitive or inductive sensors thereby forming a respective magnetic, capacitive or inductive contact-less sensing arrangement. Capacitive, magnetic or inductive sensors allow an arrangement of the body 5 of the sensor device 2 in a non-overlapping configuration with the third and fourth apertures 13A, 13B of the housing. Hence, a manual reading of the gauge window 14-1 is unobstructed or unobscured.

Figure 4:
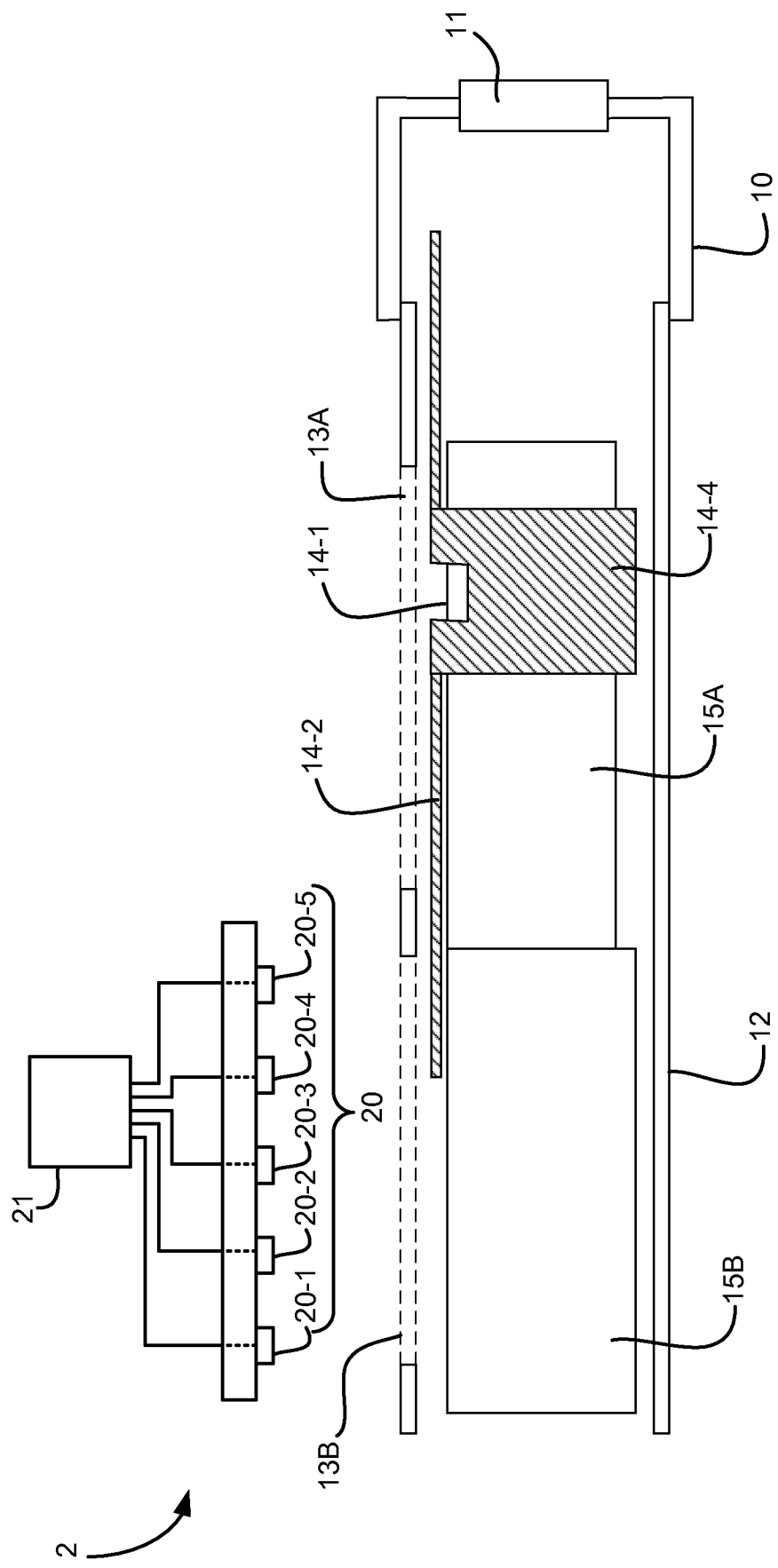
FIG. 4 shows is a simplified cut-away view of the drug delivery device components depicted in FIG. 2D in combination with part of a sensor device according to various embodiments of the disclosure.

FIG. 4 shows an extremely simplified cut-away view of the components of the delivery device 1 as depicted in FIG. 2D and a simplified schematic illustration of a sensor device 2 for use with a delivery device 1 such as that described with reference to FIGS. 1 to 2D.

The sensor device 2 comprises an array 20 of axial sensors 20-1 to 20-5 arranged such that, when the sensor device 2 is in place on the drug delivery device 1, each axial sensor 20-1 to 20-5 in the array 20 is operable to the axial position of a detectable indicator 100 that is attached to or which is embedded in the gauge element 14 as shown in FIG. 6D. The sensors 20-1 to 20-5 may be implemented as optical sensor to detect light received from a different location along an externally visible path defined by one of the at least one window 13A, 13B. Each sensor 20-1 to 20-5 may output a signal indicative of an axial position of the gauge element 14. The sensor device 2 further comprises circuitry 21 configured to receive the signals output from the optical sensors 20-1 to 20-5 of the array 20 and, based on the received signals, to determine information associated with a location along the path defined by the window 13A, 13B of the movable gauge element 14. The circuitry 21 may be further configured to control operation of the array 20.

The optical sensors 20-1 to 20-5 may be substantially equidistantly spaced from one another along a length generally corresponding to the length of the visible path. The length over which the optical sensors 20-1 to 20-5 are spaced may not be exactly the same as the length of the visible path along which the gauge element 14 moves but may be dependent on the length of the visible path with which the sensor device 2 is designed to be used.

In some embodiments, the array 20 of optical sensors 20-1 to 20-5 extends generally along an axis which, when the sensor device 2 is coupled to the delivery device 1, is generally parallel with the axis along which the moveable gauge element 14 is configured to move. The axis along which the array 20 of optical sensors extends is therefore also generally parallel with the longitudinal axis of the window 13A, 13B.

The rotation of the number sleeve 65 is proportional to the axial movement of the movable gauge element 14.

The array 20 may comprise the same number of axial sensors 20-1 to 20-5 as the number of complete rotations of the rotatable element 65A that are required to move the movable gauge element 14 from its initial to final position. The sensors 20-1 to 20-5 may be distributed adjacent the visible path of the movable gauge element such that after every complete rotation of the rotatable element 65A, the output of a successive optical sensor in the array 20 changes. For instance, after the first complete rotation of the rotatable element number sleeve 65, the output of the first sensor 20-1 in the array 20 changes from LOW to HIGH. After the second rotation, the output of the second sensor 20-2 changes from LOW to HIGH. After the third complete rotation, the output of the third sensor 20-2 changes from LOW to HIGH and so on until the fifth complete rotation at which point the output of the fifth sensor 20-5 changes from LOW to HIGH. It will thus be appreciated that the signals output by the sensors of the array 20 can be used to determine the number of complete rotations.

The code 660 read by the sensing arrangement 23 is then used by the circuitry 21 to determine the extent of any partial rotations of the number sleeve 65 number sleeve 65. The determined extent of partial rotation of the number sleeve 65 is then combined with the determined number of complete rotations to determine the currently dialed dose of the drug delivery device 1.

FIG. 7 is a simplified schematic block diagram of a sensor device 2 according to various embodiments. As described above, the sensor device 2 comprises the array 20 of optical sensors 20-1 to 20-5 which are configured to output signals to the circuitry 21. The device also 2 comprises the sensing arrangement 23 which is configured to output signals indicative of the encoded information to the circuitry 21.

The circuitry 21 may be of any suitable composition and may comprise any combination of one or more processors and/or microprocessors 210 (for simplicity, hereafter referred to as "the at least one processor") suitable for causing the functionality described herein to be performed. The circuitry 21 may additionally or alternatively comprise any combination of one or more hardware-only components such as ASICs, FPGAs etc. (which are not shown in FIG. 7).

The circuitry 21 may further comprise any combination of one or more non-transitory computer readable memory media 211, such as one or both of ROM and RAM, which is coupled to the at least one processor 210. The memory 211 may have computer-readable instructions 211A stored thereon. The computer readable instructions 210, when executed by the at least one processor 210 may cause the sensor device 2 to perform the functionality described in this specification, such as controlling operation of the array 20 and sensing arrangement 23 and interpreting the signals received therefrom.

The sensing arrangement 23 comprises at least a light source 23-2 and a photosensor 23-1. The light source 23-2 is for illuminating the encoded information 66 that is visible within the further window 63 formed in the device housing 62. The photosensor 23-1 is configured read the encoded information by detecting an image (which includes the encoded information 660) which is visible to the photosensor (i.e. which underlies the photosensor). The image is detected by detecting the light reflected back from different parts of the surface(s) on which the image is provided. The encoded information 660 is then passed to the circuitry 21. The sensing arrangement 23 may comprise further non-electrical components, which are not shown on FIG. 7. These non-electrical components of the sensing arrangement 23 are described with reference to FIG. 8.

The sensor device 2 may further comprise one or both of a display screen 24 (such as an LED or LCD screen) and a data port 25. The display screen 24 may be operable under the control of the circuitry 21 to display information regarding operation of the drug delivery device 1 to the user. For instance, the information determined by the sensor device 2 may be displayed to the user. The information determined by the sensor device 2 may include the dialed dose. Other information which can be determined by the sensor device 2 includes the drug being dispensed, the mode of the drug delivery device 1, 6, and or a history of previously-dispensed doses.

The data port 25 may be used to transfer stored information relating to the operation of the drug delivery device 6 from the memory 211 to a remote device such a PC, tablet computer, or smartphone. Similarly, new software/firmware may be transferred to the sensor device via the data port 25. The data port 25 may be a physical port such as a USB port or may be a virtual, or wireless, port such as an IR, WiFi or Bluetooth transceiver.

The sensor device 2 may further comprise a removable or permanent (preferably rechargeable with e.g. photovoltaic cells) battery 26 for powering the other components of the device 2. Instead of the battery 26, a photovoltaic or capacitor power source may be used. Other electrical components which are not shown in FIG. 7, but which may nonetheless be included in the sensor device 2 include a trigger buffer 27-1, a regulator 27-2, a voltage suppressor 27-3 and a charger chip 27-4, for charging the rechargeable battery if present.

FIG. 8 shows an example of a physical arrangement of the components of the sensor device of FIG. 7. The sensors 20-1 to 20-5 of the array 20 are arranged on a first surface of a PCB 28-1 in a way that is determined by the shape of the visible path of the movable element 14 with which the sensor device 2 is designed to be used. In the examples described herein, the visible path is linear and, consequently, the optical sensors 20-1 to 20-5 of the array 20 are linearly arranged on the PCB 28-1. When the sensor device 2 is attached to the drug delivery device 1, 6, the first surface of the PCB 28-1 faces the at least one window 13A, 13B of the drug delivery device 1, 6.

One or more of: the light source 23-2 of the sensor arrangement 23, the at least one processor 210, the memory 211, the charger chip 27-4, the voltage suppressor 27-3, the regulator 27-2 and the trigger buffer 27-1 may also be provided on the first surface of the PCB 28-1.

The screen 24 is provided on the opposite side of the PCB to the 28-1 to the array 20 of optical sensors 20-1 to 20-5, such that it is visible to the user when the sensor device 2 is attached to the drug delivery device 1, 6. The sensor device 2 may be configured so as to extend over the entire area of the at least one window 13A, 13B such that the at least one window 13A, 13B is not visible to the user when the sensor device 2 is attached.

The photosensor or detector 23-1 of the sensing arrangement 23 may not be provided on the PCB 28-1. Instead, the photosensor 23-1 may be provided on a support element 28-2 which extends from the PCB 28-1. In the example of FIG. 1, the support element 28-2 extends perpendicularly from the PCB, such that when it is attached to the drug delivery device 6, it wraps around a side of the device 1.

As will be appreciated the exact physical arrangement of the components within the sensor device 2 may not be crucial as long as, when the sensor device 2 is attached to the drug delivery device 1, the array 20 of sensors is aligned parallel to the extension of the gauge element 14 and parallel to the travel path of the gauge element 14.

For the sensing arrangement 23, it may also be important that the photosensor 23-1 of the sensing arrangement 23 is positioned so as to overlie the first aperture 63 formed in the housing 12 of the drug delivery device 6.

The sensing arrangement 23, in this example, further comprises a light guide 23-3 for guiding the light from the light source 23-2 to the first aperture 63 of the drug delivery device 1. The sensing arrangement 23 also comprises a lens array 23-4 for focussing on the photosensor 23-1 the light reflected back from the surface(s) underlying the photosensor 23-1. Put another way, the lens array 23-4 is configured to focus the image, which is provided on the surface(s) underlying the photosensor 23-1, on to the photosensor 23-2.

FIG. 9 shows the sensor device 2, without a housing, in position on the drug delivery device 1, 6. Although not shown, the sensor device 2 may be configured to be removably attached in position on the drug delivery device 1. For instance, the housing (not shown) of the sensor device 2 may include a coupling mechanism for securely affixing the sensor device 2 to the drug delivery device 1. Alternatively, any other means for securing the sensor device 2 in position on the drug delivery device 1 may be used.

As discussed above, the encoded information that is read by the sensing arrangement 23 may include a portion of the non-visible code 66 for enabling the circuitry 21 to determine the rotational orientation of the number sleeve 65. However, in some embodiments, other operational information may alternatively or additionally be included in the code 660 that is read by the sensing arrangement. For instance, the code 660 may include a portion for indicating the drug that is being delivered. This can be seen in FIGS. 10A and 10B which show examples of two different views of the encoded information that may be visible to the photosensor 23-1 of the sensing arrangement 23. At least part of the code information 660, e.g. some code lines 661, 662, 663 or code columns 671, 672, 673 may be visible through the first aperture 63 of the drug delivery device 1.

The code 660 may further include a portion, such mode indicator 680, a particular code line 661, 662, 663 or a particular code column 671, 672, 673 for indicating an actual operation mode of the drug delivery device 1, e.g. a dialing mode or delivery mode. When the device 1 is in the dialing mode, a mode indicator 680 is not part of the encoded information and when the device in the delivery mode, the mode indicator 680 is part of the encoded information 660.

Consequently, by determining whether or not the mode indicator 680 is present in the encoded information 660, the circuitry 21 can determine the mode of the device 1.

Figure 11:
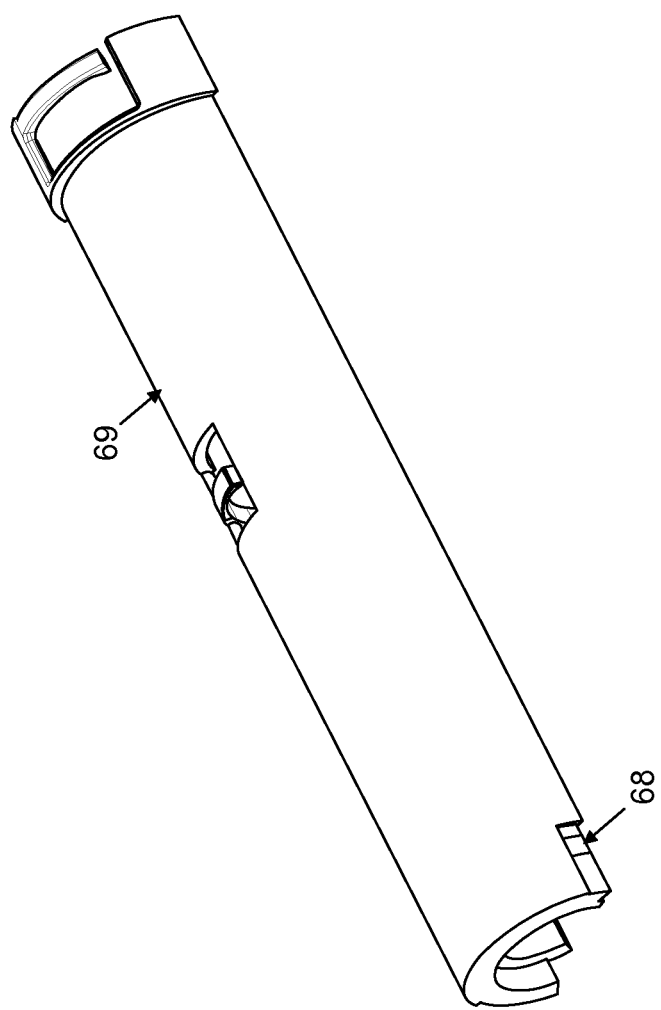
FIG. 11 is a schematic view of an internal movable element configured as a locking locking arm.

The mode indicator 680 may be provided on an internal element that is caused to move in response to actuation of the drug delivery mechanism (for instance by pushing the button 11). The movable internal element and drug delivery mechanism are together configured such that actuation of the drug delivery mechanism thereby to switch from dialing mode to delivery mode, causes the mode indicator 680 to become visible (or to disappear from) within the first aperture 63. An example of such an internal movable element 69 is shown in FIG. 11 and is a "locking arm". When situated within the drug delivery device 1, the locking arm 69 is configured to move from a first position to a second position in response to actuation of the drug delivery mechanism. The locking arm 69 may be further configured to move from the second position back to the first position in response to subsequent actuation of the drug dialing mechanism. The mode indicator 680 is only visible through the aperture 63 when the locking arm 69 is in one of the first and second positions. In this way, the sensor device 2 is able to determine the mode of the drug delivery device 1 to which it is attached.

In some embodiments, the sensor device 2 is configured to store a history of dispensed drug doses. This may be carried out by storing information indicative of the currently dialed dose, when a change from dialing mode to delivery mode is detected based on the mode indicator 680. A timestamp indicative of a time at which the mode change occurred may also be stored in association with the information indicative of the dose. In addition or alternatively, information indicative of the type of the dispensed drug, which is determined based on the drug indication code portion may be stored in association with the dose information. This may be repeated each time a dose of a drug is dispensed.

Although the drug delivery devices described herein include two windows 13A, 13B through which the movable gauge element 14 is visible, it will be appreciated that sensor devices 2 according to embodiments of the disclosure may be used with drug delivery devices 1 which include only one of these windows 13A, 13B.

It should be realized that the foregoing embodiments should not be construed as limiting. Other variations and modifications will be apparent to persons skilled in the art upon reading the present application. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. A drug delivery device for setting and injecting a dose of an injectable medicament, the drug delivery device comprising:

an elongated housing extending along a longitudinal axis and having a sidewall defining at least a first aperture; and a number sleeve rotatably supported inside of the elongated housing and comprising an outer surface, wherein a first portion of the outer surface is visible through the first aperture, and wherein the number sleeve comprises a non-visible code in a region of the first portion, wherein the non-visible code is invisible to a human eye, and wherein the non-visible code is reflective in the UV spectral range of electromagnetic radiation, wherein the non-visible code is a two dimensional code having a code array with numerous code lines and code columns, wherein the code lines extend along the longitudinal axis, and wherein the code columns extend along a tangential direction on the outer surface of the number sleeve, and wherein a size of the first aperture in the tangential direction is larger than or equal to a tangential extension of two adjacently located code lines, and wherein the size of the first aperture along the longitudinal axis is larger than the size of the first aperture along the tangential direction.

2. The drug delivery device according to claim 1, wherein the non-visible code comprises a reflective microstructure on the outer surface of the number sleeve, and wherein the reflective microstructure is a reflective zero-order diffractive microstructure.

3. The drug delivery device according to claim 2, wherein at least the first portion of the outer surface is metallized or comprises a metal coating.

4. The drug delivery device according to claim 1, wherein the outer surface comprises a second portion with numerous visible symbols extending along a helical pattern.

5. The drug delivery device according to claim 4, wherein the first portion and the second portion overlap at least in sections.

6. The drug delivery device according to claim 4, wherein the non-visible code is located on top of at least one or several of the visible symbols, or wherein at least one or several of the visible symbols are located on top of the non-visible code.

7. The drug delivery device according to claim 1, further comprising a gauge element that is configured to move along an axial path that is parallel to the longitudinal axis, wherein the sidewall of the elongated housing further defines an elongated aperture, wherein the axial path extends along the elongated aperture, wherein the gauge element is movable inside of the elongated aperture, and wherein the gauge element comprises a gauge window through which the outer surface of the number sleeve is visible.

8. The drug delivery device according to claim 7, wherein the number sleeve is axially fixed inside of the elongated housing, wherein the number sleeve, located radially inside of the gauge element, is threadedly engaged with the gauge element, and wherein the gauge element is in axial slidable engagement with the elongated housing.

9. A drug delivery device according to claim 7, wherein the gauge element comprises at least one detectable indicator at a predetermined axial location.

10. The drug delivery device according to claim 1, wherein the non-visible code comprises a luminescent paint or a luminescent ink printed or coated on the outer surface of the number sleeve.

11. A sensor device removably attachable to a drug delivery device for setting and injecting a dose of an injectable medicament,
wherein the drug delivery devices comprises:
an elongated housing extending along a longitudinal axis and having a sidewall defining at least a first aperture, and
a number sleeve rotatably supported inside of the elongated housing and comprising an outer surface, wherein a first portion of the outer surface is visible through the first aperture, and wherein the number sleeve comprises a non-visible code in a region of the first portion,
wherein the non-visible code is invisible to a human eye, and
wherein the non-visible code is reflective in the UV spectral range of electromagnetic radiation
wherein the non-visible code is a two dimensional code having a code array with numerous code lines and code columns, wherein the code lines extend along the longitudinal axis, and wherein the code columns extend along a tangential direction on the outer surface of the number sleeve, and
wherein a size of the first aperture in the tangential direction is larger than or equal to a tangential extension of two adjacently located code lines; and
wherein the size of the first aperture along the longitudinal axis is larger than the size of the first aperture along the tangential direction;
wherein the sensor device comprises:
a sensing arrangement overlying the first aperture when the sensor device is attached to the drug delivery device and configured to receive optical signals from the non-visible code, and
a circuitry connected to the sensing arrangement and configured to process signals obtained from the sensing arrangement when the sensing arrangement receives optical signals,
wherein the sensing arrangement is configured to read a portion of the non-visible code through the first aperture, and wherein the circuitry is configured to determine, based on an externally visible portion of the non-visible code, an angular position of the number sleeve relative to the elongated housing and information relating to a drug dose to which the drug delivery device is currently dialled.

12. A drug delivery system comprising:
a drug delivery device for setting and injecting a dose of an injectable medicament, the drug delivery device comprising:
an elongated housing extending along a longitudinal axis and having a sidewall defining at least a first aperture, and
a number sleeve rotatably supported inside of the elongated housing and comprising an outer surface, wherein a first portion of the outer surface is visible through the first aperture, and wherein the number sleeve comprises a non-visible code in a region of the first portion, wherein the non-visible code is invisible to a human eye, and wherein the non-visible code is reflective in the UV spectral range of electromagnetic radiation; wherein the non-visible code is a two dimensional code having a code array with numerous code lines and code columns, wherein the code lines extend along the longitudinal axis, and wherein the code columns extend along a tangential direction on the outer surface of the number sleeve, and wherein a size of the first aperture in the tangential direction is larger than or equal to a tangential extension of two adjacently located code lines, and wherein the size of the first aperture along the longitudinal axis is larger than the size of the first aperture along the tangential direction; and a sensor device removably attachable to the drug delivery device, the sensor device comprising:
- a sensing arrangement overlying the first aperture when the sensor device is attached to the drug delivery device and configured to receive optical signals from the non-visible code, and
- a circuitry connected to the sensing arrangement and configured to process signals obtained from the sensing arrangement when the sensing arrangement receives optical signals,
- wherein the sensing arrangement is configured to read a portion of the non-visible code through the first aperture, and wherein the circuitry is configured to determine, based on an externally visible portion of the non-visible code, an angular position of the number sleeve relative to the elongated housing and information relating to a drug dose to which the drug delivery device is currently dialled.

13. A drug delivery device for setting and injecting of a dose of an injectable medicament, the drug delivery device comprising:
   an elongated housing extending along a longitudinal axis and having a sidewall that defines at least a first aperture and an elongated aperture, the elongated aperture extending along the longitudinal axis;
   a number sleeve rotatably supported inside of the elongated housing and comprising an outer surface, wherein a first portion of the outer surface is visible through the first aperture, and wherein the number sleeve comprises a non-visible code in a region of the first portion; and
   a gauge element movable inside of the elongated aperture and configured to move along an axial path that is parallel to the longitudinal axis, wherein the gauge element comprises a gauge window through which the outer surface of the number sleeve is visible.

14. The drug delivery device according to claim 13, wherein an extension of the code lines along the longitudinal direction is at least twice as large as the tangential extension of a code line.

15. A drug delivery device for setting and injecting of a dose of an injectable medicament, the drug delivery device comprising:
   an elongated housing extending along a longitudinal axis and having a sidewall with at least a first aperture;
   a number sleeve rotatably supported inside of the housing and comprising an outer surface, wherein a first portion of the outer surface is visible through the first aperture, and wherein the number sleeve comprises a non-visible code in a region of the first portion; and
   a gauge element that is configured to move along an axial path that is parallel to the longitudinal axis, wherein the sidewall of the elongated housing further defines an elongated aperture, wherein the axial path extends along the elongated aperture, wherein the gauge element is movable inside of the elongated aperture, and wherein the gauge element comprises a gauge window through which the outer surface of the number sleeve is visible.

16. The drug delivery device according to claim 15, wherein the number sleeve is axially fixed inside of the elongated housing, wherein the number sleeve, located radially inside of the gauge element, is threadedly engaged with the gauge element, and wherein the gauge element is in axial slidable engagement with the elongated housing.

17. The drug delivery device according to claim 15, wherein the gauge element comprises at least one detectable indicator at a predetermined axial location.

* * * * *